(12) United States Patent
Higashi et al.

(10) Patent No.: US 11,718,590 B2
(45) Date of Patent: Aug. 8, 2023

(54) COMPOUND, DERIVATIZATION REAGENT, AND METHOD FOR SYNTHESIZING COMPOUND

(71) Applicants: TOKYO UNIVERSITY OF SCIENCE FOUNDATION, Tokyo (JP); JEOL Ltd., Tokyo (JP)

(72) Inventors: Tatsuya Higashi, Tokyo (JP); Shoujiro Ogawa, Tokyo (JP); Masaki Takiwaki, Tokyo (JP); Seketsu Fukuzawa, Tokyo (JP)

(73) Assignees: TOKYO UNIVERSITY OF SCIENCE FOUNDATION, Tokyo (JP); JEOL Ltd., Tokyo (JP)

( * ) Notice: Subject to any disclaimer, the term of this patent is extended or adjusted under 35 U.S.C. 154(b) by 0 days.

(21) Appl. No.: 17/557,751

(22) Filed: Dec. 21, 2021

(65) Prior Publication Data
US 2022/0204459 A1   Jun. 30, 2022

(30) Foreign Application Priority Data

Dec. 24, 2020 (JP) .................................. 2020-214897
Oct. 7, 2021 (JP) .................................. 2021-165742

(51) Int. Cl.
*C07D 249/12* (2006.01)
(52) U.S. Cl.
CPC .................................. *C07D 249/12* (2013.01)
(58) Field of Classification Search
CPC .................................................. C07D 249/12
See application file for complete search history.

(56) References Cited

PUBLICATIONS

Ogawa et al.; A novel Cookson-type reagent for enhancing sensitivity and specificity in assessment of infant vitamin D status using liquid chromatography/tandem mass spectrometry; Rapid Communication in Mass Spectrometry; 2013; vol. 27; pp. 2453-2460.
Ishige et al.; Improved sensitivity of serum/plasma 1α,25-dihydroxyvitamin D quantification by DAPTAD derivatization; Clinica Chimica Acta; 2017; vol. 473; pp. 173-179.
Extended European Search Report issued in EP21215693.9 dated May 11, 2022.
Ogawa et al., Comparative evaluation of new Cookson-type reagents for LC/ESI-MS/MS assay of 25-hydroxyvitamin D3 in neonatal blood samples, Biomedical Chromatography, Jun. 1, 2016, vol. 30, No. 6, pp. 938-945.

*Primary Examiner* — Shawquia Jackson
(74) *Attorney, Agent, or Firm* — The Webb Law Firm

(57) ABSTRACT

A compound represented by Chemical formula 1:

[Chemical formula 1]

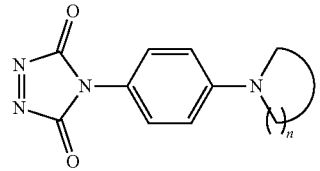

(100)

wherein n is an integer of 2 or more, is provided. Also provided is a derivatization reagent for derivatizing a diene-containing compound, including a compound represented by Chemical formula 1. Further provided is a synthesis method for a compound, including a nucleophilic substitution reaction between an aryl halide and a heterocyclic amine compound being saturated, the compound being represented by Chemical formula 1.

3 Claims, 2 Drawing Sheets

[Fig. 1]
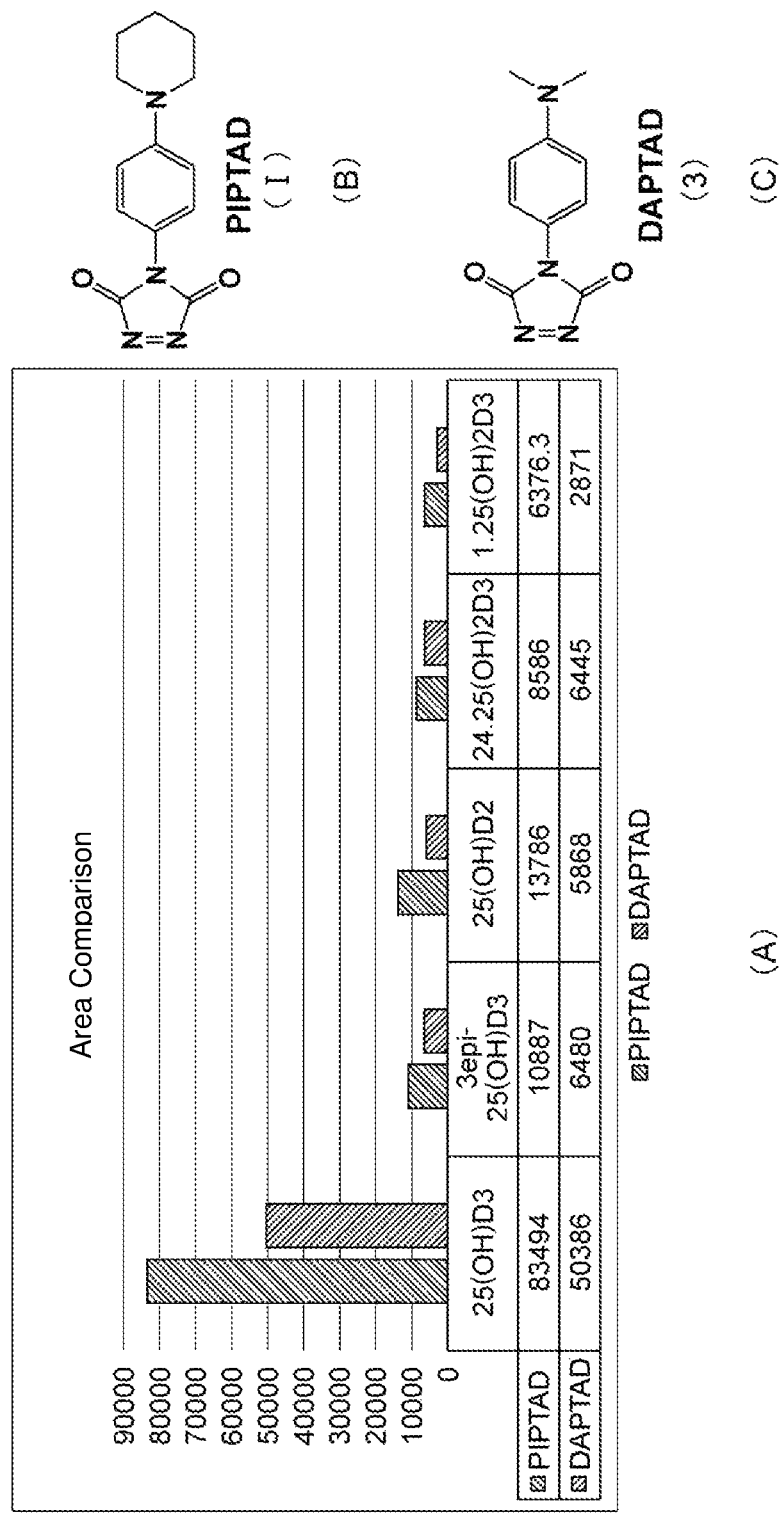

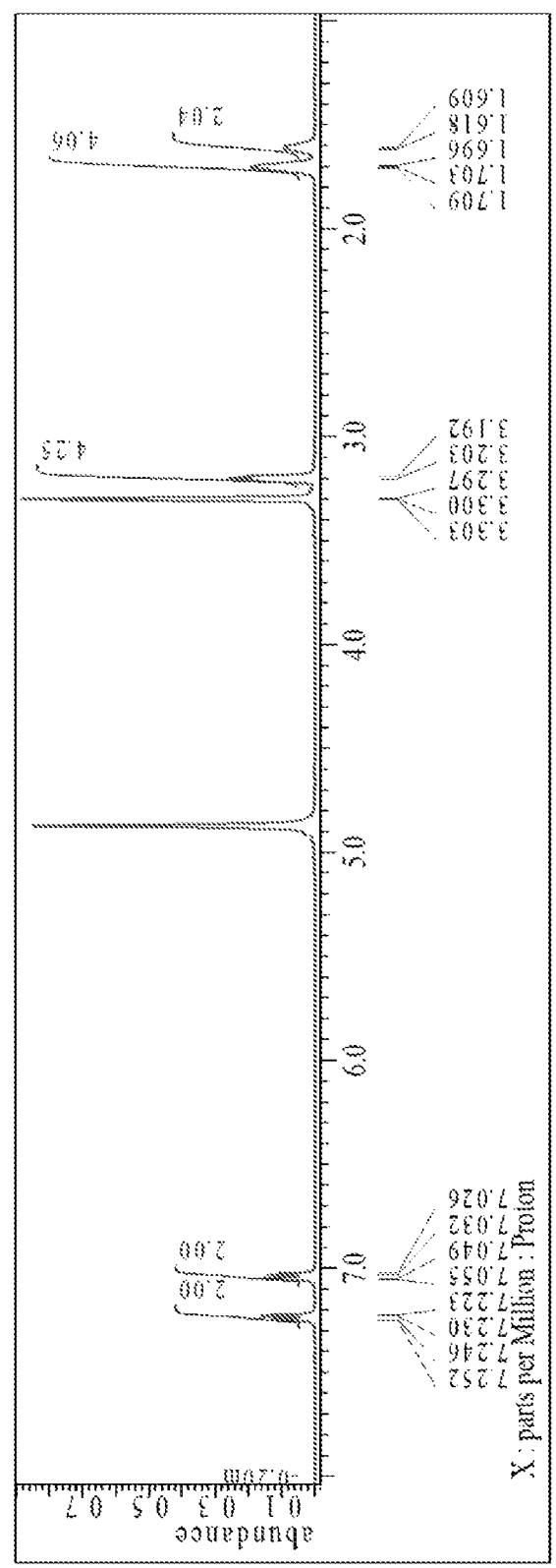
[Fig. 2]

COMPOUND, DERIVATIZATION REAGENT, AND METHOD FOR SYNTHESIZING COMPOUND

CROSS-REFERENCE TO RELATED APPLICATIONS

This application claims priority to Japanese Patent Application Nos. 2020-214897 filed Dec. 24, 2020 and 2021-165742 filed Oct. 7, 2021, the disclosures of which are hereby incorporated by reference in their entirety.

BACKGROUND OF THE INVENTION

Field of the Invention

The present invention relates to a compound, a derivatization reagent, and a method for synthesizing a compound.

Description of Related Art

In the quantification of vitamin D metabolites, analysis using a liquid chromatography tandem mass spectrometer (hereinafter, also referred to as "LC/MS/MS") equipped with a tandem mass spectrometer (hereinafter, also referred to as "MS/MS") has been widespread. Then, the ionization efficiency and chromatographic separation are known to be improved by derivatization with a derivatization reagent. The derivatization reagent used here has a 1,2,4-triazoline-3,5-dione structure.

Regarding derivatization methods for vitamin D metabolites, for example, 4-[4-dimethylaminophenyl]-1,2,4-triazoline-3,5-dione (DAPTAD) has been proposed (see Non-Patent Literature 1). According to a derivatization method for vitamin D metabolites, the diene moiety of a vitamin D metabolite (vitamin D may be included) is subjected to a Diels-Alder reaction to form a derivative of the vitamin D metabolite.

CITATION LIST

Non-Patent Literature

[Non-Patent Literature] Rapid Commun., Mass Spectrum., 2013, 27, 2453-2460

SUMMARY OF INVENTION

Technical Problem

However, with the technique proposed in Non-Patent Literature 1, further improvement in the sensitivity of detection of vitamin D metabolites may not be achieved.

Thus, the present invention has been made in light of such circumstances, and a first object thereof is to provide: a compound capable of achieving further improvement in the sensitivity of detection of vitamin D metabolites; a derivatization reagent for derivatizing a vitamin D metabolite, which contains such a compound; and a method for synthesizing such a compound.

Then, in the present invention, the range of analysis targets is not limited to vitamin D metabolites, and the range of analysis targets can be extended to diene-containing compounds. Therefore, a second object of the present invention is to provide: a compound capable of achieving further improvement in the sensitivity of detection of diene-containing compounds; a derivatization reagent for derivatizing a diene-containing compound, which contains such a compound; and a method for synthesizing such a compound.

Solution to Problem

Extensive research was conducted to achieve the above objects, and as a result, surprisingly, successfully developed: a compound capable of achieving further improvement in the sensitivity of detection of diene-containing compounds (in particular, vitamin D metabolites can be mentioned); a derivatization reagent for derivatizing a diene-containing compound (in particular, vitamin D metabolite can be mentioned), which contains such a compound; and a method for synthesizing such a compound. The present invention has thus been accomplished.

That is, in a first aspect, the present invention provides a compound represented by the following general formula (100).

[Chemical formula 1]

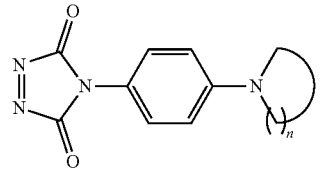

(100)

In the above general formula (100), n is an integer of 2 or more.

In the compound of the first aspect according to the present invention, the compound represented by general formula (100) may be a compound represented by the following formula (I).

[Chemical formula 2]

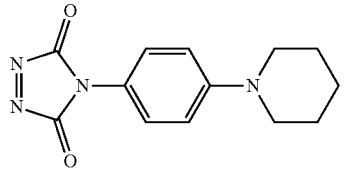

(I)

In addition, in a second aspect, the present invention provides a derivatization reagent for derivatizing a diene-containing compound, which contains a compound represented by the following general formula (100).

[Chemical formula 3]

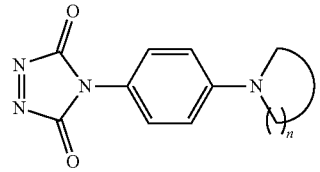

(100)

In the above general formula (100), n is an integer of 2 or more.

In the derivatization reagent of the second aspect according to the present invention, the compound represented by general formula (100) may be a compound represented by the following formula (I).

[Chemical formula 4]

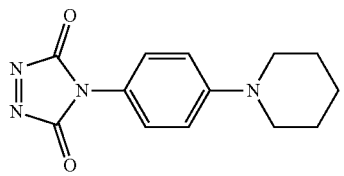

(I)

Further, in a third aspect, the present invention provides a method for synthesizing a compound represented by the following general formula (100), which includes a nucleophilic substitution reaction between an aryl halide and a saturated heterocyclic amine compound.

[Chemical formula 5]

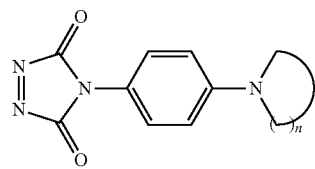

(100)

In the above general formula (100), n is an integer of 2 or more.

Further, in the synthetic method of the third aspect according to the present invention, the compound represented by general formula (100) may be a compound represented by the following formula (I), and the saturated heterocyclic amine compound may be piperidine.

[Chemical formula 6]

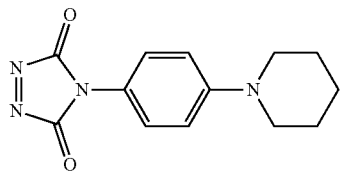

(I)

Advantageous Effects of Invention

According to the present invention, it is possible to achieve further improvement in the sensitivity of detection of diene-containing compounds (in particular, vitamin D metabolites can be mentioned). Incidentally, the effects described here are not necessarily limited, and any of the effects described herein may be applied.

BRIEF DESCRIPTION OF DRAWINGS

FIG. 1 is a diagram showing the analysis results of a PIPTAD derivative of a vitamin D metabolite and a DAPTAD derivative of a vitamin D metabolite.

FIG. 2 is a diagram showing NMR spectral data of 1,2,4-triazolidine-3,5-dione (VIII).

DESCRIPTION OF THE INVENTION

Hereinafter, preferred embodiments for carrying out the present technology will be described. The embodiments described below show some examples of typical embodiments of the present technology, and do not narrow the interpretation of the scope of the present technology.

1. Outline of the Present Invention

First, the outline of the present invention will be described. The present invention relates to a compound, a derivatization reagent for derivatizing a diene-containing compound (in particular, vitamin D metabolite), and a method for synthesizing such a compound.

Conventionally, in order to detect and quantify active vitamin D (e.g., 1,25-dihydroxyvitamin $D_3$, 1,25$(OH)_2D_3$) present in trace amounts in living organisms, concentration using an antibody column is required (e.g., see Non-Patent Literature, Clinica Chimica Acta 2017, 473, 173-179). However, the derivatization reagent DAPTAD is less sufficient in sensitivity, and, for more accurate quantification, the development of a derivatization reagent that is more sensitive than DAPTAD has been desired. For example, 1,25$(OH)_2D_3$ is an important metabolite that occupies the center of the physiological action of vitamin D, and its accurate quantification is thus in great demand.

The present invention has been made in light of the above circumstances. The present invention is for high-sensitivity detection of vitamin D metabolites in the field of clinical examination, especially using mass spectrometry, and can be used regardless of manufacturer of mass spectrometer. In order to allow quantification of vitamin D metabolites by mass spectrometry to become widespread in the field of clinical examination in the future, it is essential that the same value can be obtained anytime and anywhere regardless of manufacturer of the device. The present invention supports such spread by improving the detection sensitivity and thus bridging the gap among different manufacturers' models.

Hereinafter, preferred modes for carrying out the present invention will be described in detail. The embodiments described below show some examples of typical embodiments of the present invention, and do not narrow the interpretation of the scope of the present invention.

2. First Embodiment (Example 1 of Compound)

The compound of a first embodiment according to the present invention (Example 1 of Compound) is a compound represented by the following general formula (100) (4-cycloalkylaminophenyl-1,2,4-triazoline-3,5-dione).

[Chemical formula 7]

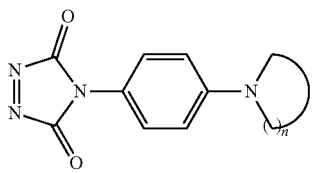

(100)

In general formula (100), n is an integer of 2 or more.

The compound represented by general formula (100) is preferably a compound represented by the following formula (I). The compound represented by formula (I) is a compound represented by general formula (100), wherein n =5 (6-membered saturated heterocycle), and is 4-[4-(1-piperidinyl)phenyl]-1,2,4-triazoline-3,5-dione (PIPTAD).

[Chemical formula 8]

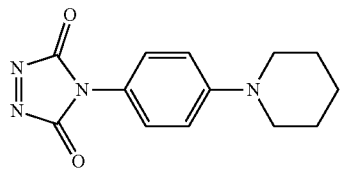

(I)

3. Second Embodiment (Example of Derivatization Reagent)

The derivatization reagent of a second embodiment according to the present invention (Example of Derivatization Reagent) is a derivatization reagent for derivatizing a diene-containing compound, which contains a compound represented by the following general formula (100). Then, the derivatization reagent containing a compound represented by the following general formula (100) is a Cookson-type derivatization reagent.

[Chemical formula 9]

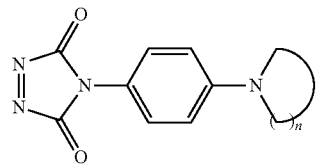

(100)

In general formula (100), n is an integer of 2 or more.

The derivatization reagent of the second embodiment according to the present invention is a reagent for derivatizing a diene-containing compound, particularly a vitamin D metabolite in a biological specimen such as blood, serum, plasma, urine, saliva, cerebrospinal fluid, or nail, and detecting the same with high sensitivity, which is for use in quantitative analysis using a tandem mass spectrometer coupled with liquid chromatography (LC-MS/MS) Like this, the reagent for derivatization provided by the present invention may be used for derivatizing a diene-containing compound contained in a biological specimen. The biological specimen is not limited to those listed above, and may be a liquid component or a solid component contained in organisms (particularly mammals, more particularly humans).

Then, the diene-containing compound quantitatively reacts, through a Diels-Alder reaction, with the compound represented by general formula (100) contained in the derivatization reagent of the second embodiment according to the present invention, and is derivatized. Thus, for example, in quantitative analysis by LC/ESI (electrospray ionization)-MS/MS, the diene-ontaining compound (e.g., vitamin D metabolite) can be detected with high sensitivity and high selectivity.

The compound represented by general formula (100) is preferably a compound represented by the following formula (I). The compound represented by formula (I) is a compound represented by general formula (100), wherein n=5 (6-membered saturated heterocyclic structure), and is 4-[4-(1-piperidinyl)phenyl]-1,2,4-triazoline-3,5-dione (PIPTAD).

[Chemical formula 10]

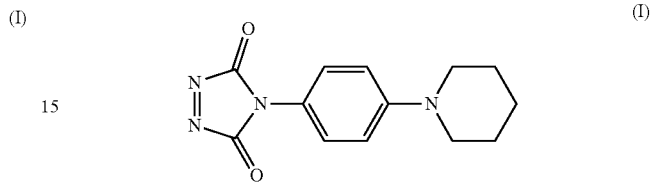

(I)

Hereinafter, the diene-containing compound to be derivatized will be described in detail.

As diene-containing compounds, for example, s-cis-diene-containing compounds, s-trans-diene-containing compounds, and the like can be mentioned. Incidentally, in a case where an s-trans-diene-containing compound is derivatized using a derivatization reagent containing the compound represented by general formula (100) described above (e.g., PIPTAD) or a derivatization reagent containing the compound represented by general formula (100-1) described below, it is necessary to perform a pre-heat treatment to isomerize the s-trans-diene-containing compound to an s-cis-diene-containing compound.

Next, specific examples of s-cis-diene-containing compounds will be described. Examples of s-cis-diene-containing compounds include, but are not particularly limited to, steroids, vitamin D, and vitamin D metabolites.

Of s-cis-diene-containing compounds, steroids are not particularly limited. They are not limited to naturally occurring compounds and may also be synthetic products or analogs thereof. For example, 7-dehydrocholesterol, ergosterol, conjugated linoleic acid, vitamin A, and the like can be mentioned.

Of s-cis-diene-containing compounds, "vitamin D" belongs to secosteroids in a broad sense, and is a general term for vitamin D2 derived from vegetable foods and vitamin D3 derived from animal foods and skin production. The two are homologues that differ only in the side chain structure, and are considered to be similarly metabolized in a human body and have the same level of physiological activity. Therefore, as used herein, the two are not distinguished and may be simply referred to as vitamin D. In addition, as used herein, vitamin D and vitamin D metabolites may be simply referred to as vitamin D. Such a term means any molecular species associated with naturally occurring or synthesized vitamin D, or with vitamin D produced by the conversion of vitamin D, such as intermediates and products of vitamin D metabolism.

As such molecular species of vitamin D (vitamin D metabolites), for example, 25-hydroxyvitamin $D_3$ (25(OH)$D_3$), 25-hydroxyvitamin $D_2$ (25(OH)$D_2$), 1α,25-dihydroxyvitamin $D_3$ (1,25(OH)$_2D_3$), 1α,25-dihydroxyvitamin $D_2$ (1,25(OH)$_2D_2$), 23,25-dihydroxyvitamin $D_3$ (23,25(OH)$_2$ $D_3$), 25,26-dihydroxyvitamin $D_3$ (25,26(OH)$_2D_3$), 24,25-dihydroxyvitamin $D_3$ (24,25(OH)$_2D_3$), 4β,25-dihydroxyvitamin $D_3$ (4β,25(OH)$_2D_3$), 25-hydroxyvitamin $D_3$-23,26-lactone (25(OH)$D_3$Lactone), 1α,25-dihydroxyvitamin $D_3$-23,26-lactone (1,25(OH)$_2D_3$Lactone), and the like can be mentioned, but molecular species are not limited to them. The molecular species of vitamin D may be isomers of the above molecular species. For example, 3-epi-25-hydroxyvitamin $D_3$ (3-epi-25(OH)$D_3$) and the like can be mentioned. In addition, these vitamin D molecular species may also be sulfates. For example, 25-hydroxyvitamin $D_3$-33-sulfate (25(OH)$D_3$S), 25-hydroxyvitamin $D_3$-33-glucuronic acid (25(OH)$D_3$Gluc), and the like can be mentioned. Upon the quantitative analysis of vitamin D, several kinds of such molecular species of vitamin D (vitamin D metabolites) may be contained.

For example, the reaction formula of a derivatization reaction between 25(OH)$D_3$ and PIPTAD is as follows.

[Chemical formula 12]

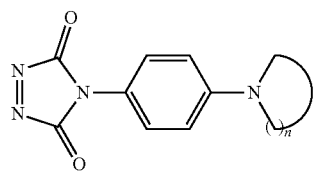

(100)

In general formula (100), n is an integer of 2 or more.

[Chemical formula 11]

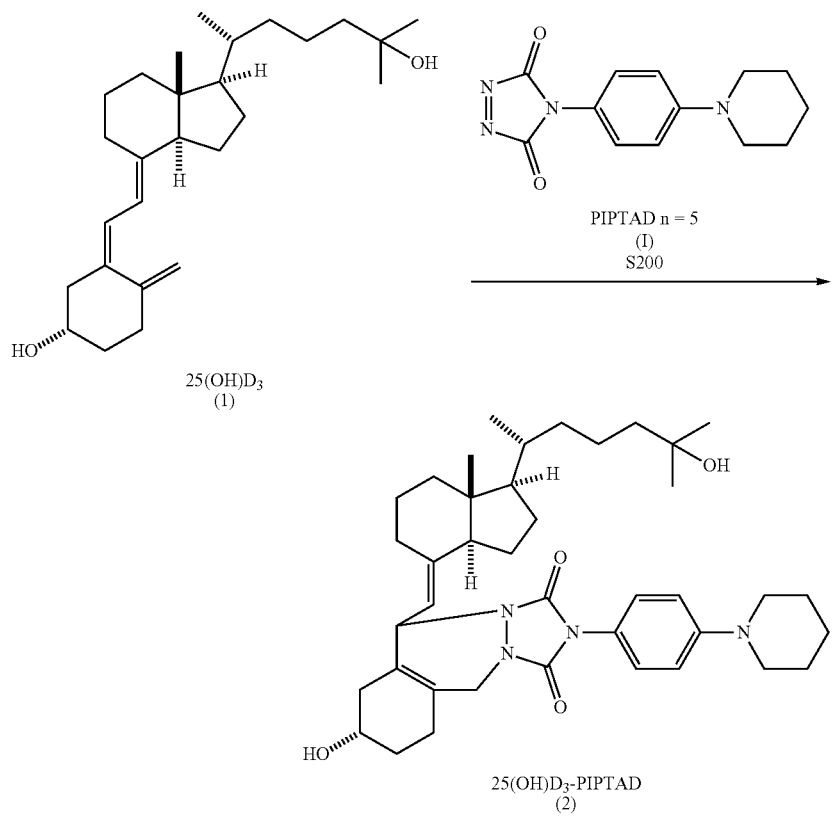

In step S200, PIPTAD (I) is added to the s-cis-diene moiety of 25(OH)$D_3$ (1) to form a 25(OH)$D_3$-PIPTAD derivative (2). In the 25(OH)$D_3$-PIPTAD derivative (2), the electron density of the nitrogen atom increases due to the electron-donating effect of the alkyl group. Accordingly, protons are added more easily, and ionization takes place more easily.

4. Third Embodiment (Example of Method for Synthesizing Compound)

The method for synthesizing a compound of a third embodiment according to the present invention (Example of Method for Synthesizing Compound) is a method for synthesizing a compound represented by the following general formula (100), wherein the method comprises a nucleophilic substitution reaction between an aryl halide and a saturated heterocyclic amine compound.

The compound represented by general formula (100) is preferably a compound represented by the following formula (I). The compound represented by formula (I) is a compound represented by general formula (100), wherein n=5 (6-membered saturated heterocycle), and is 4-[4-(1-piperidinyl)phenyl]-1,2,4-triazoline-3,5-dione (PIPTAD).

In the nucleophilic substitution reaction in the method for synthesizing a compound represented by formula (I), piperidine is used as the saturated heterocyclic amine compound. Then, in the nucleophilic substitution reaction in the method for synthesizing a compound represented by formula (I), methyl p-fluorobenzoate is preferably used as the aryl halide.

[Chemical formula 13]

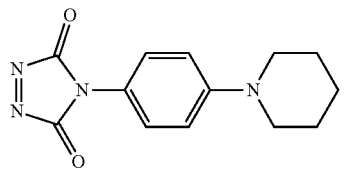

(I)

5. Fourth Embodiment (Example 2 of Compound)

The compound of a fourth embodiment according to the present invention (Example 2 of Compound) is a compound represented by the following general formula (100-1).

[Chemical formula 14]

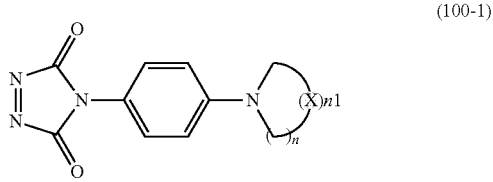

(100-1)

In general formula (100-1), X is an N (nitrogen) atom, a P (phosphorus) atom, an O (oxygen) atom, or an S (sulfur) atom. In general formula (100-1), n is an integer of 1 or more, and n1 is an integer of 1 or more.

Similarly to the compound of the first embodiment according to the present invention (Example 1 of Compound), a reagent containing a compound represented by general formula (100-1) can derivatize a diene-containing compound. Specific examples of diene-containing compounds are as described above.

Similarly to the method for synthesizing a compound represented by general formula (100) described above, the method for synthesizing a compound represented by general formula (100-1) can include a nucleophilic substitution reaction between an aryl halide and a saturated heterocyclic amine compound.

6. Examples

Hereinafter, the effects and the like of the present invention will be described in detail with reference to examples. Incidentally, the scope of the present invention is not limited to the examples.

6-1. Example 1

[Synthesis of 4-[4-(1-piperidinyl)phenyl]-1,2,4-triazoline-3,5-dione (PIPTAD (I))]

Based on the following scheme, 4-[4-(1-piperidinyl)phenyl]-1,2,4-triazoline-3,5-dione (PIPTAD (I)) was synthesized.

[Chemical formula 15]

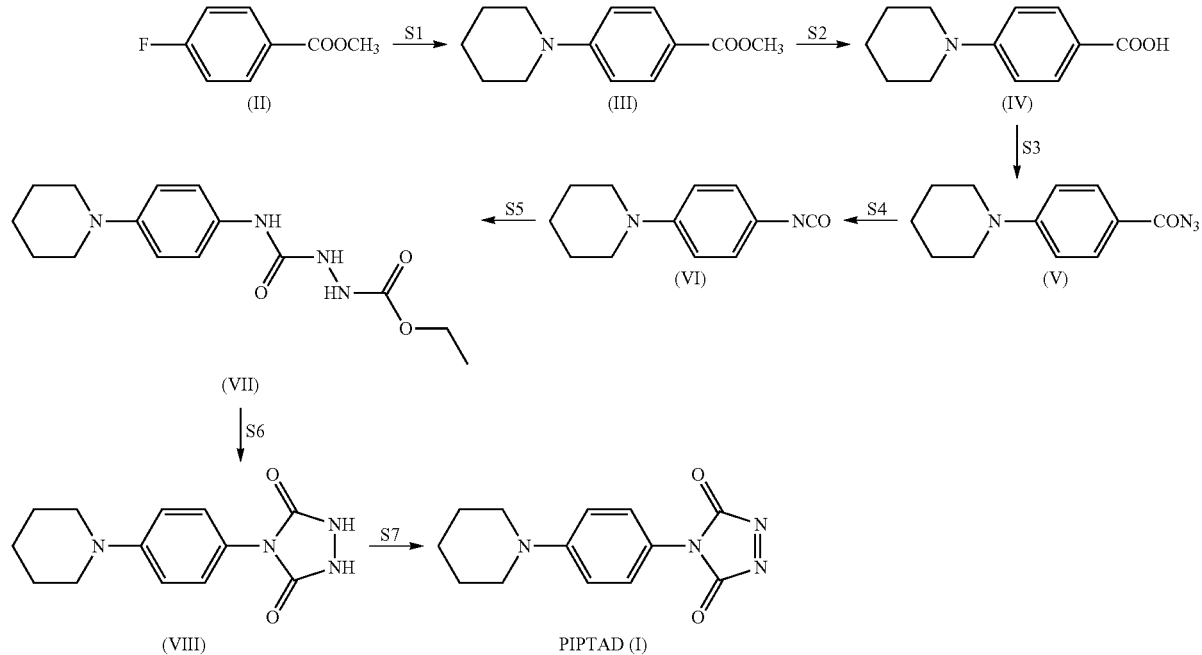

1. Synthesis of methyl 4-(1-piperidinyl)benzoate (III) [Step S1]

Methyl p-fluorobenzoate (II) (256 μL, 2 mmol) was dissolved in toluene (5 mL), and potassium carbonate (140 mg, 1.0 mmol) and piperidine (311 μL, 6.0 mmol) were added, followed by heating under reflux for 12 hours. The reaction mixture was diluted with ethyl acetate (25 mL) and washed with brine (25 mL×2). The organic layer was dried over magnesium sulfate (MgSO$_4$), and the solvent was removed under reduced pressure, thereby giving methyl 4-(1-piperidinyl)benzoate (III) as a colorless solid (403 mg, 1.8 mmol).

2. Synthesis of 4-(1-piperidinyl)benzoic acid (IV) [Step S2]

Methyl 4-(1-piperidinyl) benzoate (III) (360 mg, 1.6 mmol) and sodium hydroxide (100 mg, 2.5 mmol) were mixed using 10 mL of a 50% aqueous methanol solution and stirred at 100° C. overnight. The solvent was removed under reduced pressure, and the residue was dissolved in 2 mL of water. Next, the solution was ice-cooled and acidified by adding 10% hydrochloric acid. The precipitated, colorless powder of 4-(1-piperidinyl)benzoic acid (IV) was suction-filtered while being thoroughly washed with cold water and thus collected (290 mg, 1.4 mmol).

3. Synthesis of 4-(1-piperidinyl)benzoic acid azide (V) [Step S3]

4-(1-Piperidinyl)benzoic acid (IV) (205 mg, 1.0 mmol) was dissolved in DMF (1 mL), and DPPA (265 µL, 1.2 mmol) and triethylamine (500 µL) were added dropwise, followed by stirring with ice-cooling for 1.5 hours. The reaction mixture was diluted with ethyl acetate (25 mL) and washed with brine (25 mL×3). The organic layer was dried over magnesium sulfate (MgSO$_4$), the solvent was distilled off under reduced pressure, and then the residue was subjected to silica gel column chromatography (150×12 mm i.d.) packed with Wakogel® 60N (particle size: 63 to 212 µm). Hexane-ethyl acetate (9:1, v/v) eluted fractions were collected, and the solvent was removed under reduced pressure, thereby giving 4-(1-piperidinyl)benzoic acid azide (V) as a colorless solid (170 mg, 0.74 mmol).

4. Synthesis of 4-(1-piperidinyl)phenylsemicarbazide (VII) [Step S4 and Step S5]

4-(1-piperidinyl)benzoic acid azide (V) (170 mg, 0.74 mmol) was dissolved in toluene (2 mL) and refluxed for 20 minutes to convert into a compound (VI) [Step S4]. Without isolating the compound (VI), a benzene solution (1 mL) of ethyl carbazate (110 mg, 1.1 mmol) was added to the reaction mixture. The mixture was stirred at room temperature for 1 hour and then refluxed for another 1 hour. After being allowed to cool, the produced precipitate was suction-filtered while being washed with cold toluene, thereby giving 4-(1-piperidinyl)phenylsemicarbazide (VII) as a colorless solid (210 mg, 0.69 mmol).

5. Synthesis of 4-[4-(1-piperidinyl)phenyl]-1,2,4-triazolidine-3,5-dione (VIII) [Step S6]

An aqueous solution (5 mL) of potassium carbonate (90 mg, 0.64 mmol) was added to 4-(1-piperidinyl)phenylsemicarbazide (VII) (100 mg, 0.32 mmol) and stirred at 90° C. for 3 hours. Acetic acid was added to the reaction mixture while checking the pH with a universal pH test paper to adjust the pH to around 6. After the solvent was removed under reduced pressure, the residue was subjected to ODS column chromatography (300×10 mm i.d.) packed with Wakogel® 100C18 (particle size: 63 to 212 µm). MeOH-water (3:7, v/v) eluted fractions were collected, and the solvent was removed under reduced pressure, followed by recrystallization with water, thereby giving a colorless solid of 4-[4-(1-piperidinyl)phenyl]-1,2,4-triazolidine-3,5-dione (VIII) (48 mg, 0.18 mmol).

$^1$H-NMR (CD$_3$OD) δ 7.24 (d, J=9.0 Hz, 2H), 7.04 (d, J=9.0 Hz, 2H), 3.20 (m, 4H), 1.70 (m, 4H), 1.61 (m, 2H) (FIG. 2).

6. Synthesis of 4-[4-(1-piperidinyl)phenyl]-1,2,4-triazoline-3,5-dione (PIPTAD) (I) [Step S7]

4-[4-(1-Piperidinyl)phenyl]-1,2,4-triazolidine-3,5-dione (VIII) (2 mg) was suspended in ethyl acetate (10 mL), and iodobenzenediacetate (3 mg) was added, followed by stirring at room temperature for 3 hours. The reaction mixture was centrifuged (1,000 g, 10 min), and the supernatant was stored as an ethyl acetate solution of 4-[4-(1-piperidinyl) phenyl]-1,2,4-triazoline-3,5-dione (PIPTAD) (I) (2 µg/10 µL). Incidentally, this solution was stored at -18° C.

6-2. Example 2

[Analysis of vitamin D metabolites with 4-[4-(1-piperidinyl) phenyl]-1,2,4-triazoline-3,5-dione (PIPTAD (I)) (PIPTAD (I))]

To each of the five vitamin D metabolite components (25(OH)D$_3$, 3-epi-25(OH)D$_3$, 25(OH)D$_2$, 24,25(OH)$_2$D$_3$, and 1.25(OH)$_2$D$_3$) concentrated to dryness, 100 µL of an ethyl acetate solution of PIPTAD (I) (2 µg/10 µL) was added, and allowed to stand at room temperature for 30 minutes. 20 µL of ethanol was added to stop the reaction, followed by nitrogen gas purge to dryness. After redissolution in 100 µL of a 50% acetonitrile solution, 10 µL was analyzed using LC-MS/MS.

Incidentally, as comparative examples, for each of the five vitamin D metabolite components (25(OH)D$_3$, 3-epi-25 (OH)D$_3$, 25(OH)D$_2$, $_{24,25}$(OH)$_2$D$_3$, and 1,25(OH)$_2$D$_3$), an ethyl acetate solution of DAPTAD (3) (4-[4-dimethylaminophenyl]-1,2,4-triazoline-3,5-dione) (2 µg/10 µL) was used.

For example, the reaction formula of the derivatization reaction between 25(OH)D$_3$ and DAPTAD is as follows.

[Chemical formula 16]

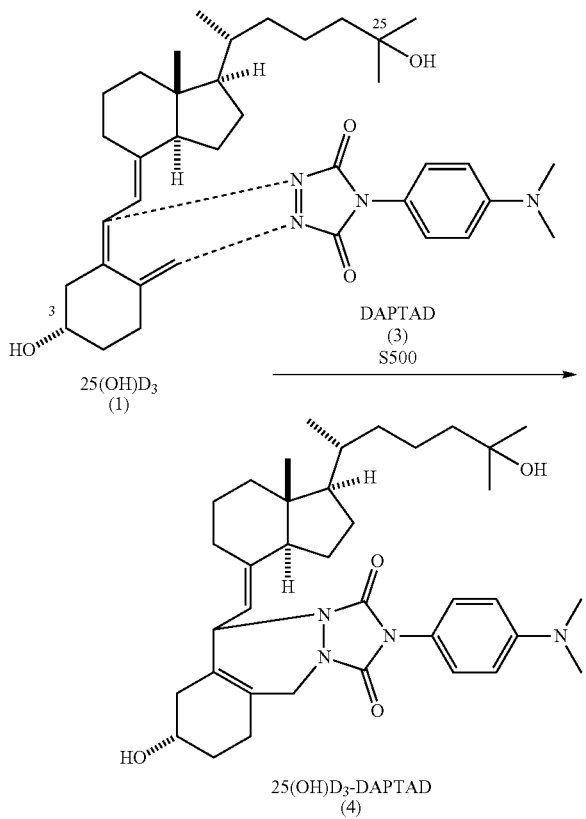

In Step S500, DAPTAD (3) is added to the s-cis-diene moiety of 25(OH)D$_3$ (1) to form a 25(OH)D$_3$-DAPTAD derivative (4).

For LC/MS/MS, the ACQUITY UPLC I-Class system manufactured by Nihon Waters K.K. was connected to the Xevo TQ-XS triple quadrupole mass spectrometer and used.

(LC Analysis Conditions)

The analysis column is C18 series. The LC analysis conditions in the case where the analysis targets are 25(OH)D$_3$, 3-epi-25(OH)D$_3$, 25(OH)D$_2$, and 24,25(OH)$_2$D$_3$ are as shown below in Table 1, while the LC analysis conditions in the case where the analysis target is 1,25(OH)$_2$D$_3$ are as shown below in Table 2.

(MS/MS Analysis Conditions)

The ionization conditions are ESI (electrospray ionization) positive, and the analysis targets (PIPTAD derivatives of the above five vitamin D metabolite components and DAPTAD derivatives of the above five vitamin D metabolite components) and MRM parameters are as shown below in Table 3.

Incidentally, for data analysis, QuanLinx, an automated processing system in Waters® MassLinx 4.1 Software, was used.

TABLE 1

Four Vitamin D Metabolite Components (25(OH)D$_3$, 3-epi—25(OH)D$_3$, 25(OH)D$_2$, and 24,25(OH)$_2$D$_3$)
Mobile phases A: Water + 0.1% formic acid
B: Acetonitrile + 0.1% formic acid

|  | Time (min) | Flow Rate (mL/min) | A(%) | B(%) |
|---|---|---|---|---|
| Gradient Profile | initial | 0.5 | 70 | 30 |
|  | 1 | 0.5 | 44 | 56 |
|  | 3 | 0.5 | 44 | 56 |
|  | 3.5 | 0.5 | 35 | 65 |
|  | 3.67 | 0.5 | 10 | 90 |
|  | 4.67 | 0.5 | 10 | 90 |
|  | 4.68 | 0.5 | 70 | 30 |
|  | 6 | 0.5 | 70 | 30 |

TABLE 2

1,25(OH)$_2$D$_3$
Mobile phases A: Water + 0.1% formic acid
B: Acetonitrile + 0.1% formic acid

|  | Time (min) | Flow Rate (mL/min) | A(%) | B(%) |
|---|---|---|---|---|
| Gradient Profile | initial | 0.4 | 50 | 50 |
|  | 0.5 | 0.4 | 50 | 50 |
|  | 0.51 | 0.4 | 35 | 65 |
|  | 1.8 | 0.4 | 35 | 65 |
|  | 1.81 | 0.4 | 10 | 90 |
|  | 2.8 | 0.4 | 10 | 90 |
|  | 2.81 | 0.4 | 50 | 50 |
|  | 4 | 0.4 | 50 | 50 |

TABLE 3

MRM Parameters

| Analyte | MRM(m/z) | Cone Voltage(kv) | CE(eV) |
|---|---|---|---|
| 25(OH)D3-DAPTAD | 619.4 > 341.1 | 48 | 28 |
| 3epi-25(OH)D3-DAPTAD | 619.4 > 341.1 | 48 | 28 |
| 25(OH)D2-DAPTAD | 631.4 > 341 1 | 48 | 28 |

TABLE 3-continued

MRM Parameters

| Analyte | MRM(m/z) | Cone Voltage(kv) | CE(eV) |
|---|---|---|---|
| 24,25(OH)2D3-DAPTAD | 635.4 > 341.1 | 48 | 28 |
| 1,25(OH)2D3-DAPTAD | 635.4 > 357.2 | 48 | 28 |
| 25(OH)D3-PIPTAD | 659.4 > 381.1 | 30 | 30 |
| 3epi-25(OH)D3-PIPTAD | 659.4 > 381.1 | 30 | 30 |
| 25(OH)D2-PIPTAD | 671.4 > 381.1 | 30 | 30 |
| 24,25(OH)2D3-P1PTAD | 675.4 > 381.1 | 30 | 30 |
| 1,25(OH)2D3-PIPTAD | 675.6 > 397.4 | 30 | 30 |

6-3. Analysis Results

The analysis results are shown in FIG. 1. The horizontal axis of FIG. 1 shows, from left to right, the 25(OH)D$_3$-PIPTAD derivative, 25(OH)D$_3$-DAPTAD derivative, 3-epi-25(OH)D$_3$-PIPTAD derivative, 3-epi-25(OH)D$_3$-DAPTAD derivative, 25(OH)D$_2$-PIPTAD derivative, 25(OH)D$_2$-DAPTAD derivative, 24,25(OH)$_2$D$_3$-PIPTAD derivative, 24,25(OH)$_2$D$_3$-DAPTAD derivative, 1,25(OH)$_2$D$_3$-PIPTAD derivative, and 1,25(OH)$_2$D$_3$-DAPTAD derivative. The vertical axis shows the ionic strength.

FIG. 1 shows the results of the ionic strength comparison (Area comparison) between the derivative with PIPTAD and the derivative with DAPTAD of each of the five vitamin D metabolite components (25(OH)D$_3$, 3-epi-25(OH)D$_3$, 25(OH)D$_2$, 24,25(OH)$_2$D$_3$, and 1,25(OH)$_2$D$_3$).

As shown in FIG. 1, the ionic strength of the 25(OH)D$_3$-PIPTAD derivative was 83494, and the ionic strength of the 25(OH)D$_3$-DAPTAD derivative was 50386. That is, for 25(OH)D$_3$, PIPTAD achieved an about 1.7-fold sensitivity improvement compared to DAPTAD.

As shown in FIG. 1, the ionic strength of the 3-epi-25(OH)D$_3$-PIPTAD derivative was 10887, and the ionic strength of the 3-epi-25(OH)D$_3$-DAPTAD derivative was 6480. That is, for 3-epi-25(OH)D$_3$, PIPTAD achieved an about 1.7-fold sensitivity improvement compared to DAPTAD.

As shown in FIG. 1, the ionic strength of the 25(OH)D$_2$-PIPTAD derivative was 13786, and the ionic strength of the 25(OH)D$_2$-DAPTAD derivative was 5868. That is, for 25(OH)D$_2$, PIPTAD achieved an about 2.3-fold sensitivity improvement compared to DAPTAD.

As shown in FIG. 1, the ionic strength of the 24,25(OH)$_2$D$_3$-PIPTAD derivative was 8586, and the ionic strength of the 24,25(OH)$_2$D$_3$-DAPTAD derivative was 6445. That is, for 24,25(OH)$_2$D$_3$, PIPTAD achieved an about 1.3-fold sensitivity improvement compared to DAPTAD.

As shown in FIG. 1, the ionic strength of the 1,25(OH)$_2$D$_3$-PIPTAD derivative was 6376.3, and the ionic strength of the 1,25(OH)$_2$D$_3$-DAPTAD derivative was 2871. That is, for 1,25(OH)$_2$D$_3$, PIPTAD achieved an about 2.2-fold sensitivity improvement compared to DAPTAD.

Incidentally, the present invention is not limited to the above embodiments and the above examples, and various modifications can be made without departing from the gist of the present invention.

In addition, the effects described herein are merely exemplary and not restrictive, and there may also be other effects.

In addition, the present invention may also be configured as follows.

[1]

A compound represented by the following general formula (100):

[Chemical formula 17]

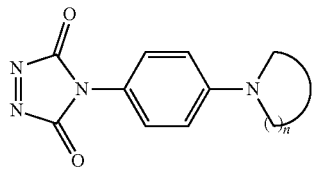
(100)

(in the general formula (100), n is an integer of 2 or more).

[2]

The compound according to [1], wherein the compound represented by general formula (100) is a compound represented by the following formula (I):

[Chemical formula 18]

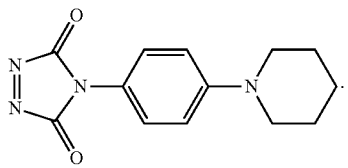
(I)

[3]

A derivatization reagent for derivatizing a diene-containing compound, containing a compound represented by the following general formula (100):

[Chemical formula 19]

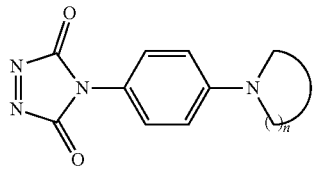
(100)

(in the general formula (100), n is an integer of 2 or more).

[4]

The derivatization reagent according to [3], wherein the compound represented by general formula (100) is a compound represented by the following formula (I):

[Chemical formula 20]

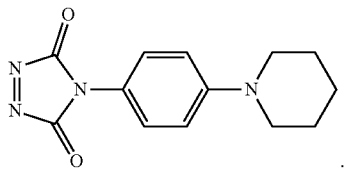
(I)

[5]

A method for synthesizing a compound, including a nucleophilic substitution reaction between an aryl halide and a saturated heterocyclic amine compound, the compound being represented by the following general formula (100):

[Chemical formula 21]

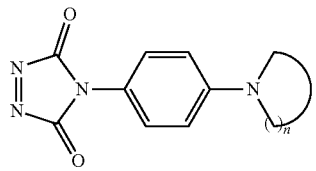
(100)

(in the general formula (100), n is an integer of 2 or more).

[6]

The synthesis method according to [5], wherein
the heterocyclic amine compound is piperidine, and
the compound represented by general formula (100) is a compound represented by the following formula (I):

[Chemical formula 22]

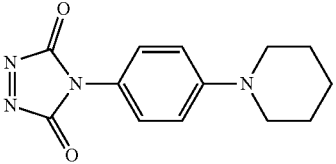
(I)

The invention claimed is:

1. A compound represented by Chemical formula 2:

[Chemical formula 2]

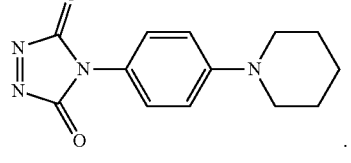

2. A derivatization reagent for derivatizing a diene-containing compound, comprising a compound represented by Chemical formula 4:

[Chemical formula 4]

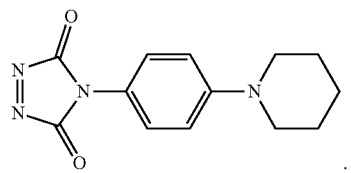

3. A synthesis method for a compound represented by Chemical formula 6:

[Chemical formula 6]
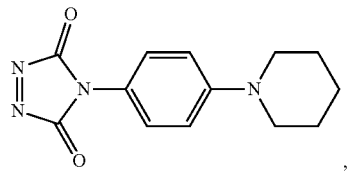
,
wherein the synthesis method comprises:
   a nucleophilic substitution reaction between p-fluorobenzoate and piperidine to obtain methyl 4-(1-piperidinyl)benzoate, and
   conversion of the methoxycarbonyl group in the methyl 4-(1-piperidinyl)benzoate into a 1,2,4-triazoline group to obtain the compound represented by Chemical formula 6.
* * * * *